United States Patent
Graham

[19]

[11] Patent Number: 5,833,459
[45] Date of Patent: Nov. 10, 1998

[54] TOOTH ISOLATOR

[76] Inventor: Neil J. Graham, 10815 Meads Ave., Orange, Calif. 92669

[21] Appl. No.: 608,464

[22] Filed: Feb. 28, 1996

[51] Int. Cl.$^6$ .................................................... A61C 5/12
[52] U.S. Cl. ........................................... 433/138; 433/136
[58] Field of Search .................................. 433/136, 137, 433/138, 139, 8; 24/3.1, 3.12, 7, 11 C, 11 HC, 11 R, 336, 343, 362; 248/74.2

[56] References Cited

U.S. PATENT DOCUMENTS

| | | | |
|---|---|---|---|
| 422,056 | 2/1890 | Martin | 24/3.1 |
| 802,483 | 10/1905 | Simmons | 433/138 |
| 1,407,474 | 2/1922 | Nielsen | 24/343 |
| 2,066,732 | 1/1937 | Kunz | 24/462 |
| 2,396,203 | 3/1946 | Robinson | 433/139 |
| 2,651,109 | 9/1953 | Kanter | 433/138 |
| 2,885,783 | 5/1959 | Golden | 433/139 |
| 2,930,128 | 3/1960 | Berens | 433/138 |
| 3,104,434 | 9/1963 | Noordhoek | 24/3.1 |
| 3,318,224 | 5/1967 | Bohanon | 24/462 |
| 4,565,526 | 1/1986 | Kawata et al. | 433/8 |
| 4,681,544 | 7/1987 | Anthony | 433/229 |

FOREIGN PATENT DOCUMENTS

| | | | |
|---|---|---|---|
| 6618260 | 7/1967 | Netherlands | 24/336 |
| 2204086 | 11/1988 | United Kingdom | 24/3.12 |

*Primary Examiner*—Ralph A. Lewis
*Attorney, Agent, or Firm*—William G. Lane

[57] ABSTRACT

A cotton roll holder adapted to removably receive a cotton roll, the combination of the holder and the cotton roll useful to position the cotton roll in the mouth between the gum and the inner wall of the mouth or cheek to isolate a tooth from the inner wall of the mouth.

32 Claims, 4 Drawing Sheets

TOOTH ISOLATOR

FIELD OF THE INVENTION

The present invention is directed to a device for positioning a cotton roll in the mouth to separate the inner lining of the mouth from the outer side of the teeth for installation of the brackets and the like for orthodontic procedures, such as installation, adjustment and repair of teeth braces.

BACKGROUND OF THE INVENTION

The orthodontic procedures for straightening teeth today involves the placement of a bracket on the external side of the teeth with an adhesive. To ensure a good adhesive bond, the tooth receiving the bracket must be dry in order to have the adhesive set and bond properly. The mouth is a wet environment and the inner surface of the mouth or cheek is separated from the gum and the tooth with one or more cotton rolls that are positioned between the gum and inner surface of the cheek. The cotton rolls have a tendency to work out of the mouth, thus permitting the wet surface of the mouth to touch the tooth and/or the bracket during the adhesive step. The surface of the mouth can move the bracket and effect the adhesive bond. There are isolators available, such as Pascal isolator, which is designed to hold two cotton rolls side by side which are positioned upright or vertically in the mouth, rather than horizontally. The Pascal device can block the area that the orthodontist is working on and restricts access to the tooth. Dentech and Garmers produce cotton roll holders. The holders are articulated type devices which hold one or two cotton rolls in the mouth. These holders have one leg extending under the chin and another leg extending into the mouth to position cotton rolls in front of and behind the gum to isolate the tooth area. These devices cannot be used for the upper teeth since the devices require opposing legs to hold the cotton rolls in the mouth. The devices are relatively big and encumber the orthodontist by occupying a large space in the mouth which has limited space to begin with. Because of their size, these devices cannot be utilized in the front of the mouth which has a sharp curvature.

SUMMARY OF THE INVENTION

The present invention is directed to a tooth isolator for holding and positioning a cotton roll in the mouth for isolating a tooth from the inner wall of the mouth or cheek during the bonding operation of an orthodontic bracket onto the tooth or other dental operation. The tooth isolator comprises a longitudinal body spine having opposing longitudinal ends and a front side and a back side; at least one pair of arms extending upwardly and outwardly from the body spine toward the front of the isolator to form a C-clamp element, the spine and arms adapted to removably receive and secure a dental cotton roll on the front side of the body spine; and at least two planar tabs extending from the back side of the body spine, the tabs are adapted to engage orthodontic brackets on teeth neighboring the tooth to be bonded to secure the cotton roll between the patient's gums and the wall of the mouth to isolate the tooth to be bonded from the wall of the mouth.

The planar tabs extending out longitudinally along the back side of the spine. The tabs can be positioned in a straight linear line or they can be positioned in a gentle longitudinal curve so as to maintain a constant distant between the teeth and the back of the spine to compensate for the curvature of the jaw line. The tabs can be fitted to the back of the spine with short posts which would make it easier to bend the tabs to align them with the teeth brackets or to break one or more tabs off the device as required.

The isolator also can be fitted with two opposing arms, conveniently located in the middle area of the spine or a pair of opposing arms located at the ends of the spine to removably receive and secure a dental cotton roll to the front side of the spine. Alternatively, the spine can be fitted with two or more spikes along its front side which can be pushed into a cotton roll to removably secure the cotton roll to the device. The back of the spine can also be fitted with one or more small hooks which are adapted to removably receive and temporarily secure the wire used in dental bracing during a bracket repair operation.

In an alternative embodiment of the present invention, the tooth isolator comprises a C-clamp element adapted to removably receive a cotton roll either in the middle or at the ends of the cotton roll. The C-clamp shaped element has a planar tab extending outwardly from its outer surface opposite the C-clamp shaped element's opening to engage a bracket on the teeth. A cotton roll will normally be fitted with two isolators, one at each end or the roll. This isolator permits the cotton roll to be bent or twisted by the orthodontic practitioner to fit the particular shape of the mouth yet still this isolator is able to maintain the cotton roll in the mouth and to isolate the tooth that is to be worked on. Preferably, the inner side of the C-clamp shaped element will have a roughened surface or a high friction surface to maintain the C-clamp on the cotton roll during use.

In another embodiment of the present invention, the tooth isolator is prepared from metal wire which is shaped to form on the back side two outward extending extension areas to engage brackets on the teeth and on the front side two C-clamp shaped elements with opposing arms at the longitudinal ends of the isolator to removably receive a cotton roll.

BRIEF DESCRIPTION OF THE DRAWINGS

FIG. 27 is a perspective view of another embodiment of a tooth isolator of the

FIG. 30 is a top view of the tooth isolator of FIG. 29;

DETAILED DESCRIPTION OF THE INVENTION

Figure 3:
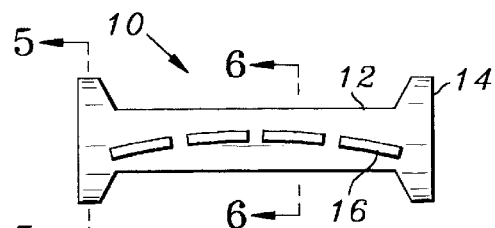
FIG. 3 is a rear plan view of the tooth isolator of FIG. 1.
Figure 4:
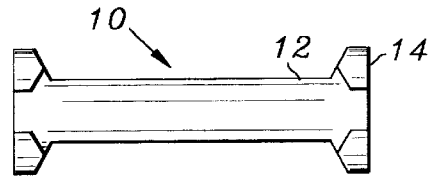
FIG. 4 is a front plan view of the tooth isolator of FIG. 1.
Figure 6:
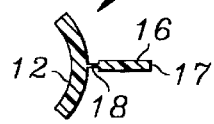
FIG. 6 is a cross sectional view taken along lines 6—6 of FIG. 3.
Figure 5:
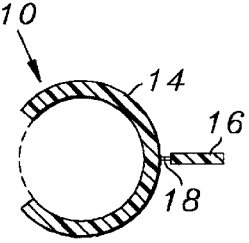
FIG. 5 is a cross sectional view taken along lines 5—5 of FIG. 3.

Referring to FIGS. 1–6, the tooth isolator 10 has a body spine or backbone 12 which extends longitudinally and is curved or bowed toward the back side. At the ends of the spine, opposing arms 14 extend out radially and upwardly from both sides of the spines to form substantially circular C-clamp elements which are adapted to removably receive a cotton roll 30. Cotton rolls 30 are longitudinal cylindrical shaped cotton elements used by dentists and orthodontic practitioners to separate the inner side of the mouth or the tongue from the teeth to be worked on. The cotton rolls are soft and moisture absorbent; they maintain the area they are positioned in relatively dry so that the dentist can work in a relatively dry environment. Extending outwardly in a common longitudinally curved plane are a plurality of planar tabs 16 (see FIG. 3). The tabs can have a straight edge 17 or a serrated or high friction edge as the tab 85 described below with respect to the isolator of FIGS. 22–26. The tabs are attached to the back of the spine by short, flexible posts 18. The posts are of such dimensions that they permits the tabs to be moved from side to side or up or down to obtain a proper fit in the mouth to maintain the isolator and the cotton roll in position. The posts also permit the dentist to easily remove or break off one or more tabs from the isolator so that the tabs will not block the area that the orthodontist is working on to reposition or attach a brace bracket to the surface of the tooth (see FIG. 7). Preferably the tabs are arranged in a gently curving longitudinal plane as shown in FIG. 3. Since the mouth is substantially curved with different radii of curvature at various places in the mouth, the curvature placement of the tabs can make it easier to fit the isolator and the cotton roll into the mouth and maintain substantially equivalent distances between the bottom side of the brace brackets 26 and the isolator. Preferably, the tooth isolator has a somewhat flexible spine 12 to permit the isolator to be bent to fit the shape of the mouth about the gum line. The isolator is conveniently manufactured from a plastic or rubber material.

Figure 7:
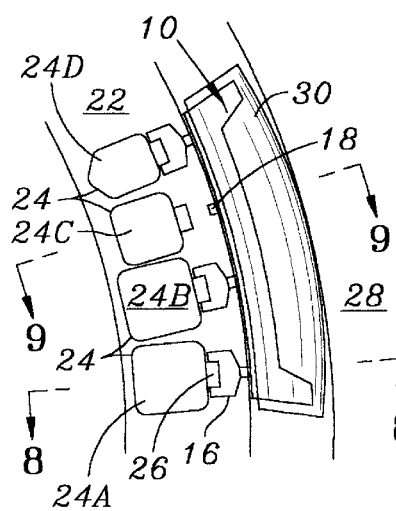
FIG. 7 is a top view of a tooth isolator positioned in a mouth.
Figure 8:
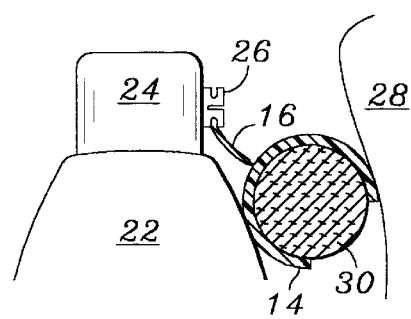
FIG. 8 is a cross sectional view taken along lines 8—8 of FIG. 7.
Figure 9:
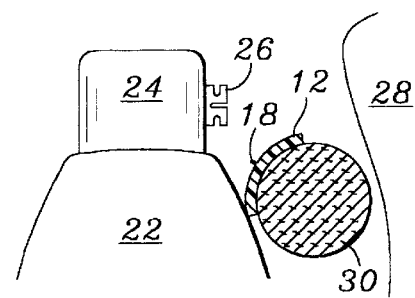
FIG. 9 is a cross sectional view taken along lines 9—9 of FIG. 7.

Referring to FIGS. 7–9, the tooth isolator 10 removably securing a cotton roll 30 is positioned in a mouth between the inner side of the mouth 28 and the outer side of the gum 22. The tab 16 opposite tooth 24C, the tooth being bonded with a bracket 26, has been broken off leaving a portion of post 18 in place. Removal of a tab gives the orthodontist maximum exposure to tooth 24C in order that the orthodontist may replace or add a bracket 26 to the external surface of the tooth or perform other dental procedures. The tabs 16 opposite the neighboring teeth 24A, 24B and 24C engage the bottom of the brackets attached to those teeth to maintain the position of the isolator and cotton roll in the mouth. The isolator maintains the cotton roll in the mouth until such time as the orthodontist has completed his work and the adhesive bonding the bracket 26 to the tooth has set (see FIGS. 8 and 9).

Figure 1:
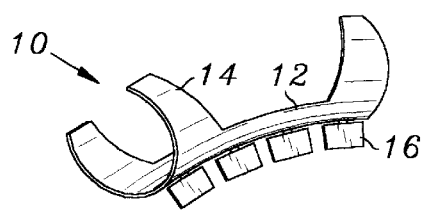
FIG. 1 is a prospective view of the tooth isolator.
Figure 2:
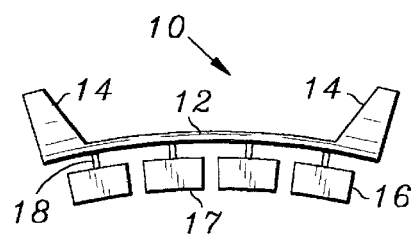
FIG. 2 is a top plan view of the tooth isolator of FIG. 1.
Figure 10:
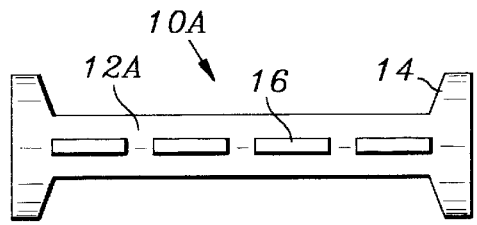
FIG. 10 is a rear plan view of a second embodiment of the tooth isolator.
Figure 11:
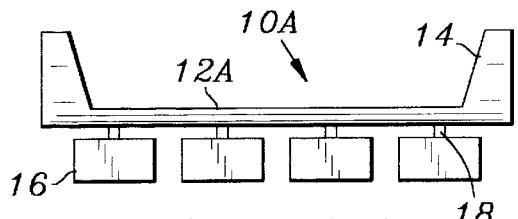
FIG. 11 is a top plan view of the tooth isolator of FIG. 10.

The isolator 10A illustrated in FIGS. 10 and 11 is very similar to the isolator 10 illustrated in FIG. 1 with the exception that the tabs 16 are arranged in a linear flat plane and the spine is straight and not curved.

Figure 12:
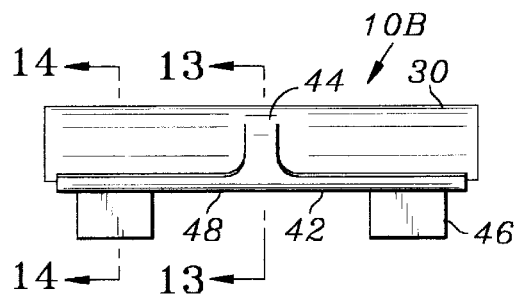
FIG. 12 is a top plan view of another embodiment of the tooth isolator.
Figure 13:
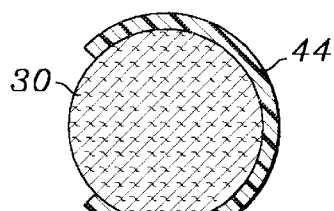
FIG. 13 is a cross sectional view taken along lines 13—13 of FIG. 12.
Figure 14:
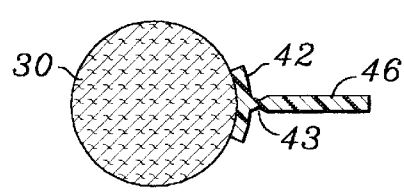
FIG. 14 is a cross sectional view taken along lines 14—14 of FIG. 12.

Referring to FIGS. 12, 13 and 14, in another embodiment of the present invention, the isolator 10B has a single set of opposing arms 44 forming a C-clamp type structure to removably receive a cotton roll 30. The arms 44 extend from the mid region of the spine 42. Extending outwardly from the back side of the spine are two planar tabs 46 which are directly connected to the spine rather than connected to the spine with posts. The area of the tab near the spine can be molded opposing grooves with relief lines to form a hinge area 43 (see FIG. 14) to make the tabs more pliable to move up and down for adjustment in the mouth. The gap 48 between the tabs 46 is positioned opposite the tooth to be worked on to give the orthodontist freedom to work and prevent the isolator from interfering with placement, positioning and bonding of a bracket on a tooth.

Figure 15:
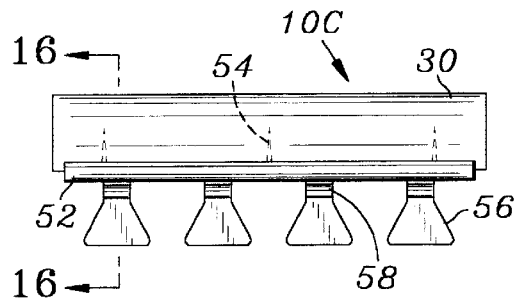
FIG. 15 is a top plan view of another embodiment of the tooth isolator of the present invention.
Figure 16:
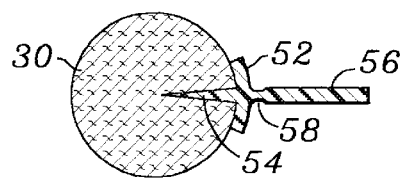
FIG. 16 is a cross sectional view taken along lines 16—16 of FIG. 15.

Referring to FIGS. 15 and 16, another embodiment of the present invention is shown wherein the tooth isolator 10C has a spine 52 with a plurality of spikes 54 extending upwardly from the front surface of the spine. The spikes can be forced into a cotton roll 30 to removably receive and secure the cotton roll to the front side of the isolator. A plurality of planer, triangular shaped tabs 56 extend outwardly from the backside of the spine. The area of the tab at the junction of the spine have hinge areas or elements 58 to make the tabs more resilient for moving up and down. Hinge elements are easily fabricated for plastic tabs by grooving or by making the hinge element 58 thinner in cross section than the tab (see FIGS. 14 and 16).

Figure 17:
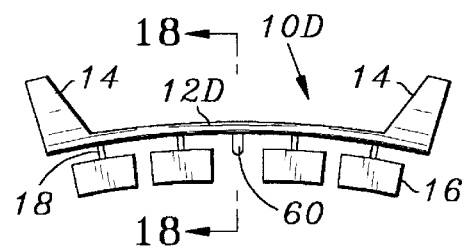
FIG. 17 is a plan top view of another embodiment of the present invention.
Figure 18:
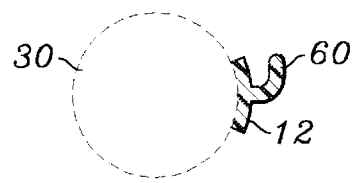
FIG. 18 is a cross sectional view taken along lines 18—18 of FIG. 17.

Referring to FIGS. 17 and 18, the tooth isolator 1 OD has a curved spine 12D that is curved or bowed toward the back side. The isolator has an outwardly extending open hook 60 on the back side of the spine which is adapted to receive on a temporary basis the wire used in braces for straightening the teeth. During repair work on brackets and during installation of brackets, the wire, which is used to straighten the teeth, is frequently in the way of the orthodontist and can be secured out of the way by the hook 60 to give the orthodontist free access to the area he or she is working on.

The curved spine 12D has a curvature similar to the curvature of the jaw to make the isolator easy to position in the mouth.

Figure 19:
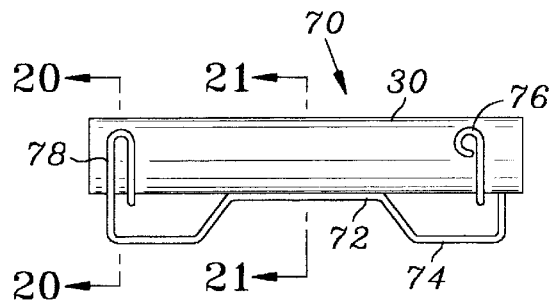
FIG. 19 is a top plan view of another embodiment of the tooth isolator.
Figure 20:
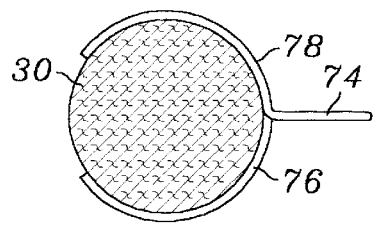
FIG. 20 is a cross sectional view taken along lines 20—20 of FIG. 19.
Figure 21:
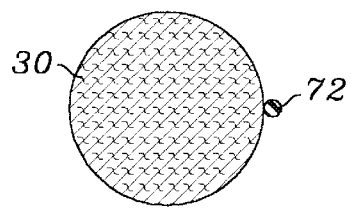
FIG. 21 is a cross sectional view taken along lines 21—21 of FIG. 19.
Figure 22:
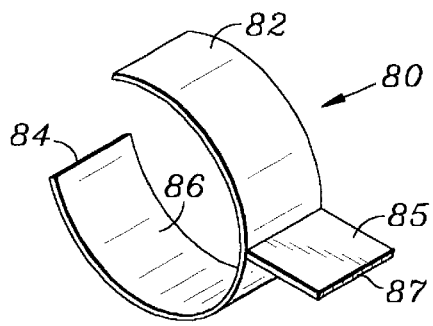
FIG. 22 is a prospective view of another embodiment of the tooth isolator of the present invention.
Figure 23:
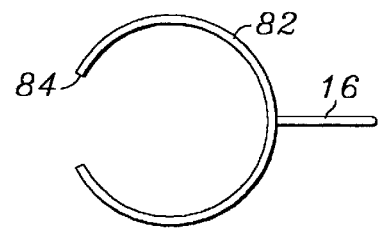
FIG. 23 is a end view of the tooth isolator of FIG. 22.
Figure 26:
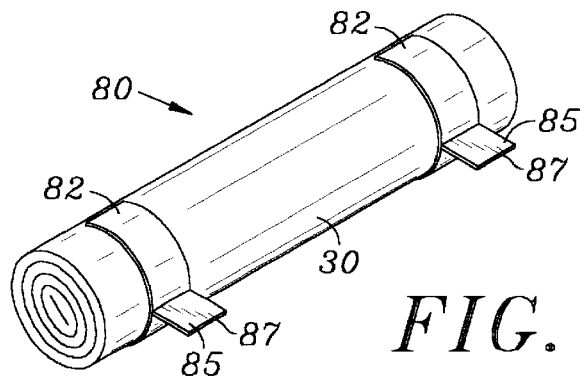
FIG. 26 is a perspective view of the tooth isolators of FIG. 22 attached to a cotton roll.
Figure 24:
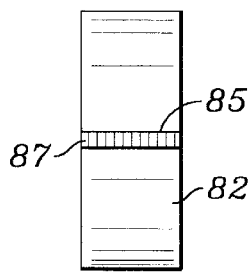
FIG. 24 is a rear plan view of the tooth isolator of FIG. 22.
Figure 25:
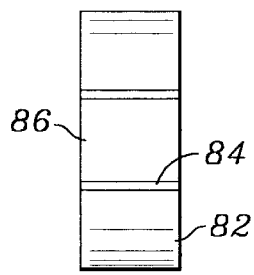
FIG. 25 is a plan front view of the tooth isolator of FIG. 22.

Referring to FIGS. 19, 20 and 21, the isolator 70 is manufactured from wire, preferably a corrosion resistant spring alloy wire. The wire is formed with the spine 72 which bows out at the opposite longitudinal ends to form tab extensions 74 which are adapted to engage brace brackets 26 in a similar fashion to the tabs 16 as shown in FIGS. 7 and 8. At each end of the spine 72, the wire is bent and doubled over to form opposing arms 7. The opposing arms 7 form a C-clamp element similar in function to the C-clamp element of the isolator shown in FIGS. 1 and 5. The middle portion of the cotton roll 30 rests against the mid section of the spine 72 and the ends of the cotton roll are removably received and secured by the opposing single stranded and double stranded arms 76 and 78 respectively (see FIG. 20).

Referring to FIGS. 22 through 26, in an alternative embodiment of the present invention, the isolator 80 has no backbone or spine and comprises a C-clamp shaped element 82 having a substantially circular cross sectional configuration with an opening 84. Opposite the opening 84 and extending from the back side or the outer side of the C-clamp shaped element 82 is a planar tab 85 adapted to engage a brace bracket 26. The planar tab 85 is normally fixed in a position and is not hinged. However, the tab 85 can be hinged in a manner similar to the manner of the tabs 46 of the isolator 10B in FIG. 12 as described above. One or more isolators 80 can be attached to a cotton roll 30. The C-clamp shaped element 82 removably receives the cotton roll 30 and secures the cotton roll in the mouth to separate the inner surface of the mouth from the tooth being worked on in a manner similar to isolator 10 in FIGS. 7 and 8. The tabs 85 engage the bottom side of the brackets 26. The ends 87 of the tabs are serrated to give the end of the tabs a non-slip or frictional surface.

In a preferred embodiment, the inner surface 86 of the isolator has a surface with a high coefficient of friction, such as a roughened surface, a surface cross hatched or a surface having protrubances to grab the surface of the cotton roll. This prevents the isolator from being rotated about the cotton roll after the isolator receives the cotton roll. Similarly, the other isolators described above can also have the inner surfaces of the opposing arms 14 and/or front side of the spine 12 treated to form a frictional surface.

Figure 27:
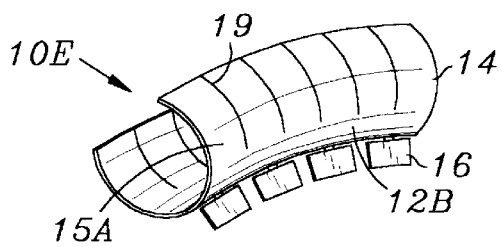
Figure 28:
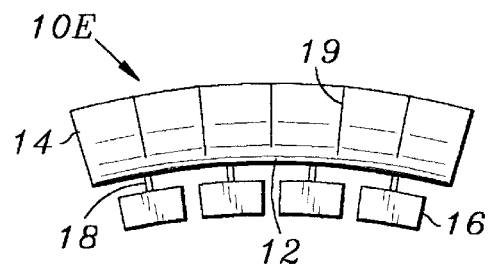
FIG. 28 is a top view of the tooth isolator of FIG. 27.

FIGS. 27 and 28 show an alternative embodiment of the present invention wherein the isolator 10E has a cylindrical body 15 comprised of a spine section 12B and a plurality of juxtaposed arms 14 extending upwardly and forwardly of the spine section 12B. Each of the arms is separated from adjoining arms by slits or small slots 19. Extending from the backside 92 of the spine section 12B are a plurality of tabs 16 which are secured to the cylindrical body by posts 18 in a manner similar to the tabs on isolator 10 of FIGS. 1–4.

Figure 29:
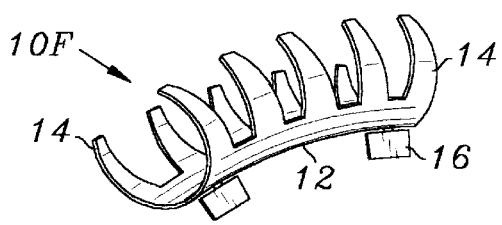
FIG. 29 is a perspective view of still another embodiment of the tooth isolator of the present invention.
Figure 30:
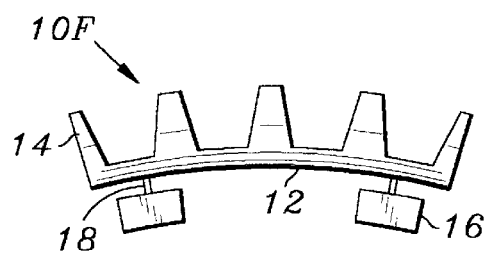
FIG. 30 is a top view of the tooth isolator of the present invention.

Another alternative embodiment of the present invention is illustrated in FIGS. 29 and 30. This isolator 10F is similar to the isolator 10 of FIGS. 1–4 with the exception that the isolator 10F of FIGS. 29 and 30 has a plurality of arms14 extending upwardly and forwardly of spine 12. In this embodiment, the isolator has only two tabs 16 positioned at either end of the spine 12 and attached to the backside 92 of the spine 12 by posts 18. The isolators described herein can have two tabs as isolator 10F of three or more tabs as described above. Isolator 10F can have more than two tabs or tabs like tabs 46 on isolator 10G described below.

Figure 31:
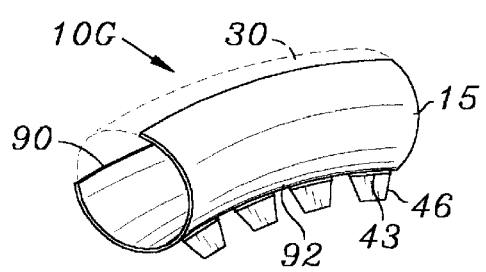
FIG. 31 is a perspective view of a further embodiment of the tooth isolator of the present invention.
Figure 32:
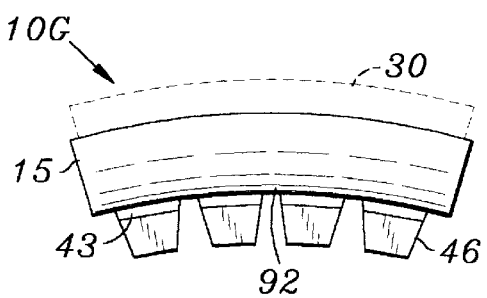
FIG. 32 is a top view of the tooth isolator of FIG. 31.

Still another embodiment of the present invention is illustrated in FIGS. 31 and 32. Isolator 10G is illustrated in these figures. Isolator 10G has a cylindrical body 15A which has an opening or longitudinal slit 90 in the front side. In a sense, cylindrical body 15 has a single set or pair of arms with each arm extending the full length of the body. Attached to and extending from the backside 92 of the cylindrical body are a plurality of planar tabs 46 which are directly connected to the spine. The area of the tab near the spine is grooved to form a hinge area 43 similar to the tabs shown in FIGS. 12, 13 and 14. The isolator is adapted to receive a cotton roll in opening 90 and to be nestled within the cylindrical body 15 (the cotton roll 30 is shown with relief lines in FIGS. 31 and 32). Isolator 10G is much stiffer that isolator 10E. In turn, isolator 10F is more flexible than isolator 10E.

The invention has been described with specific embodiments. However, the intent of the invention is to provide an isolator that will removably receive a cotton roll to position a cotton roll in the mouth to separate the portion of the mouth's inner wall from a portion of the teeth in order that an orthodontist may work on one or more teeth in a relatively dry environment. This permits the orthodontic brace bracket to be glued to the outer surface of the tooth in a moisture free environment without the inner surface of the mouth contacting the bracket before the adhesive has set.

What is claimed:

1. A tooth isolator for holding and positioning a cotton roll in the mouth for isolating a tooth from the wall of the mouth during the bonding operation of an orthodontic brace bracket onto the isolated tooth comprising:

a longitudinal body spine having opposing longitudinal ends, a front side and back side, and a longitudinal axis;

at least two separate pairs of opposing arms extending upwardly and outwardly from the front of the body spine, the body spine with the arms forming a C-shaped element, the front side of the body spine adapted to removably receive and secure a dental cotton roll; and at least two tabs extending perpendicularly outwardly from the back side of the spine, the tabs having flat sections at their remote end away from the spine, the orientation of the flat sections of the tabs lying in a plane parallel to the longitudinal axis of the spine, the tabs adapted to engage orthodontic brackets on teeth neighboring the tooth to be bonded to secure the cotton roll between the gums and the wall of the mouth to isolate the tooth to be bonded from the wall of the mouth.

2. The tooth isolator according to claim 1 wherein the spine is curved towards the back side of the spine.

3. The tooth isolator according to claim 1 wherein the isolator has one pair of opposing arms extending upwardly and outwardly from the mid portion of the body spine.

4. The tooth isolator according to claim 1 wherein the isolator has two pairs of opposing arms extending upwardly and outwardly from the body spine at each end of the body spine.

5. The tooth isolator according to claim 1 wherein the isolator has a plurality of pairs of opposing arms extending upwardly and outwardly from the body spine, the pairs positioned along the length of the body spine.

6. The tooth isolator according to claim 1 wherein the tooth isolator has four tabs.

7. The tooth isolator according to claim 1 wherein the tabs are attached to the back side of the body spine with hinge elements.

8. The tooth isolator according to claim 1 wherein each tab is connected to the back side of the body spine with a short flexible post.

9. The tooth isolator according to claim 1 wherein the isolator includes an open hook element attached to and extending outwardly from the back side of the body spine.

10. The tooth isolator according to claim 1 wherein the tabs lie in a linear longitudinal plane.

11. The tooth isolator according to claim 1 wherein the tabs lie in a longitudinal curved plane.

12. The tooth isolator according to claim 1 wherein the ends of the tabs have serrated tips adapted to engage brace brackets on teeth.

13. The tooth isolator according to claim 1 wherein the isolator has two tabs.

14. The tooth isolator according to claim 1 wherein the tooth isolator has three tabs.

15. A tooth isolator for holding and positioning a cotton roll in the mouth for isolating a tooth from the wall of the mouth during the bonding operation of an orthodontic brace bracket onto the isolated tooth comprising:

a C-shaped element having a front side, a back side, an inner surface, a longitudinal axis, and an opening on its front side which is adapted to removably receive and secure a dental cotton roll; and a flat tab extending perpendicularly outwardly from the back side from the C-shaped element, the flat tab lying in a plane parallel to the longitudinal axis of the C-shaped element, the tab attached to the back side of the body spine with hinge elements, the tab adapted to engage an orthodontic bracket on the tooth neighboring the tooth to be bonded to secure the cotton roll between the gums and the wall of the mouth to isolate the tooth to be bonded from the wall of the mouth.

16. A tooth isolator for holding and positioning cotton rolls in the mouth for isolating a tooth from the wall of the mouth during the bonding operation of an orthodontic brace bracket onto the isolated tooth comprising:

a longitudinal spine having a generally rectangular cross-section, opposing longitudinal ends and a front side and back side;

at least two spikes extending perpendicularly upwardly from the front side of the spine, the spine with the spikes adapted to penetrate the side of a dental cotton roll to removably receive and secure the dental cotton roll longitudinally parallel to and against the front side of the spine; and at least two tabs extending perpendicularly outwardly from the back side of the spine, the tabs adapted to engage orthodontic brackets on teeth neighboring the tooth to be bonded to secure the cotton roll between the gums and the wall of the mouth to isolate the tooth to be bonded from the wall of the mouth.

17. The tooth isolator according to claim 16 wherein the spine is curved towards the back side of the spine.

18. The tooth isolator according to claim 16 wherein the tabs lie in a longitudinal curved plane.

19. The tooth isolator according to claim 16 wherein the tabs are attached to the back side of the body spine with hinge elements.

20. The tooth isolator according to claim 16 wherein each tab is connected to the back side of the body spine with a short flexible post.

21. The tooth isolator according to claim 16 wherein the isolator includes an open hook element attached to and extending outwardly from the back side of the body spine.

22. The tooth isolator according to claim 16 wherein the tabs lie in a linear longitudinal plane.

23. The tooth isolator according to claim 16 wherein the ends of the tabs have serrated tips adapted to engage brace brackets on teeth.

24. The tooth isolator according to claim 16 wherein the isolator has two tabs.

25. The tooth isolator according to claim 16 wherein the tooth isolator has three tabs.

26. The tooth isolator according to claim 16 wherein the tooth isolator has four tabs.

27. A wire tooth isolator for holding and positioning a cotton roll in the mouth for isolating a tooth from the wall of the mouth during the bonding operation of an orthodontic brace bracket onto the isolated tooth comprising:

a generally longitudinal spine section formed from a wire having opposing longitudinal ends, a middle section adapted to support a cotton roll, a front side and back side;

a pair of opposing wire arm sections formed from the wire at each end of the longitudinal spine which extend upwardly and outwardly from the front side of the spine section, the spine section with the arms forming a C-shaped element on the front side of the spine section at each end of the spine section adapted to removably receive and secure a dental cotton roll; and two wire U-shaped tab sections lying in a common plane and formed from the wire extending outwardly from the back side of the spine perpendicular to the C-shaped elements, the tab sections adapted to engage orthodontic brackets on teeth neighboring the tooth to be bonded to secure the cotton roll between the gums and the wall of the mouth to isolate the tooth to be bonded from the wall of the mouth.

28. The tooth isolator according to claim 27 wherein the outer edges of the wire of the tab sections have frictional surfaces to securely engage the tabs with the bracing brackets.

29. A tooth isolator for holding and positioning a cotton roll in the mouth for isolating a tooth from the wall of the mouth during the bonding operation of an orthodontic brace bracket onto the isolated tooth comprising:

a longitudinal pliable body spine having a center portion, opposing longitudinal ends separated by the center portion, a front side and a back side, and a longitudinal axis;

a pair of opposing arms extending upwardly and outwardly from the center portion of the body spine, the body spine with the arms forming a C-shaped element, the front side of the body spine with the pair of the opposing arms adapted to removably receive and secure a dental cotton roll; and at least two tabs longitudinally spaced apart on the backside of the body spine, the tabs having outer flat sections extending perpendicularly outward from the back side of the spine, the tabs being coplanar, the orientation of the flat sections of the tabs parallel to the longitudinal axis of the spine, the tabs adapted to engage orthodontic brackets on teeth neighboring the tooth to be bonded to secure the cotton roll between the gums and the wall of the mouth to isolate the tooth to be bonded from the wall of the mouth.

30. The tooth isolator according to claim 29 wherein each arm has at least one slot perpendicular to the body spine extending from the spine to the end of the arm to separate adjacent arms.

31. A tooth isolator for holding and positioning a cotton roll in the mouth for isolating a tooth from the wall of the mouth during the bonding operation of an orthodontic brace bracket onto the isolated tooth comprising:

a C-shaped element having a front side, a back side, an inner surface, a longitudinal axis, and an opening on its front side which is adapted to removably receive and secure a dental cotton roll; and a flat tab extending perpendicularly outwardly from the back side from the C-shaped element, the flat tab lying in a plane parallel to the longitudinal axis of the C-shaped element, the tab connected to the back side of the body spine with a short flexible post, the tab adapted to engage an orthodontic bracket on the tooth neighboring the tooth to be bonded to secure the cotton roll between the gums and the wall of the mouth to isolate the tooth to be bonded from the wall of the mouth.

32. The tooth isolator according to claim 31 wherein the end of the tab has a serrated edge.

* * * * *